(12) United States Patent
Benton

(10) Patent No.: US 7,041,636 B1
(45) Date of Patent: May 9, 2006

(54) COMPOSITION FOR COUNTERACTING HAIR LOSS

(76) Inventor: Melody M. Benton, Rt. 1, Box 50, Kennard, TX (US) 75847

( * ) Notice: Subject to any disclaimer, the term of this patent is extended or adjusted under 35 U.S.C. 154(b) by 198 days.

(21) Appl. No.: 10/762,802

(22) Filed: Jan. 22, 2004

(51) Int. Cl.
*A61K 38/00* (2006.01)

(52) U.S. Cl. .......................................................... 514/2

(58) Field of Classification Search .................... 514/2
See application file for complete search history.

(56) References Cited

U.S. PATENT DOCUMENTS

| | | | |
|---|---|---|---|
| 4,670,255 A | 6/1987 | Yoshizumi et al. | |
| 6,338,855 B1 | 1/2002 | Albacarys et al. | |
| 6,379,961 B1 | 4/2002 | Carson et al. | |
| 6,511,659 B1 | 1/2003 | Mahe et al. | |
| 6,596,753 B1 | 7/2003 | Bernard et al. | |
| 2005/0089499 A1* | 4/2005 | Moussou et al. | 424/74 |

* cited by examiner

*Primary Examiner*—Bruce R. Campbell
*Assistant Examiner*—Maury Audet
(74) *Attorney, Agent, or Firm*—John F Bryan

(57) ABSTRACT

A composition for counteracting and controlling hair loss having a menthol solution combined with Polysorbate 80 or 60 and lupine protein, with the optional admixture of petroleum jelly as a thickening agent.

6 Claims, No Drawings

COMPOSITION FOR COUNTERACTING HAIR LOSS

TECHNICAL FIELD

The present invention relates generally to the field of hair care products and more particularly, to topically applied compositions used to prevent dandruff and promote hair growth.

BACKGROUND

Contemporary culture has become profoundly youth oriented. This is perhaps due to extensive public exposure of the handsome young people of stage and screen and the beautiful, forever young fashion models. Certainly, marketing demographics bias television programming for pursuit of the "under thirties". As a result of this pervasive emphasis on youth, men in general seem to feel that, when they begin to lose their hair, they are also losing their sex appeal. Another aspect of hair lose for business men is that they are well aware of the career limits imposed by age. In some cases, it may simply be a matter of resisting change but, for various reasons, men in general attempt to appear younger than their years. It is not surprising that there is a great demand for hair treatments to counteract or control hair loss, regardless of cost or inconvenience.

Formulations containing polysorbate 60, (CAS #9005-67-8) or polysorbate 80, (CAS #9005-65-6 are represented by some as being effective for promoting hair growth. Polysorbates are well known as emulsifying agents, often found in skin and hair conditioning products. Polysorbates 60 and 80 are said by some scientists to aid in removal of dihydrotestosterone (DHT), a hormone, which acts in hair follicles to inhibit production of new hair growth. Left unchecked, this action will eventuate in male pattern baldness or female hair loss.

A first object of the present inventions therefore, is to provide an effective hair treatment for counteracting or controlling hair loss. A second object is to provide such treatment in a convenient and easily usable form. A third object is to provide such treatment in a simple and inexpensive form

SUMMARY OF THE INVENTION

The present inventions contemplate a simple composition which none-the-less provides an improved treatment for counteracting and controlling hair loss. These inventions relate to or employ some steps and elements apparatus well known in the art and therefore, not the subject of detailed discussion herein.

Polysorbate 60 and polysorbate 80 have been used in hair treatment formulations, perhaps as an emulsifying cleanser, but also for its alleged ability to inhibit DHT and the negative influence it has on new hair growth. The efficacy of polysorbates for this purpose has been supported by anecdotal evidence but not, insofar as this inventor is aware, by clinical testing.

The author of the present inventions has engaged in research, and experimentation in the field of hair care products for a number of years. As a dandruff treatment, she investigated the use of polysorbate 80, procured from the Nourishair Company in the form of a thick gel. She found that, when following the suppliers recommended procedure of applying the product twenty minutes before shampooing, polysorbate 80 (P80) and, for that matter, polysorbate 60 (P60) worked well for dandruff removal in a series of trials. Based on this experience, she used the product on a number of subjects over a period of ten years.

For antiseptic purposes and tactile response, she subsequently decided to add an amount of menthol to the polysorbate 80. After experimentation with other solvents and methods, this was found to be best accomplished by dissolving menthol crystals in isopropyl alcohol and adding the solution to P80. This composition seemed to work even better for dandruff removal, so she used it in continuing trials and began selling it to others.

After a short time, a number of her subjects came back with unsolicited reports of new hair growth, suspecting that the dandruff treatment might be responsible. Upon examination, new growth, generally in the form of vellous hair, was confirmed in virtually every such instance. This experience continued, until it suddenly occurred to the author that the fine, vellous hairs might be thickened by the addition of lupine protein to the treatment. This was done by the addition of lupine protein, procured from RITA Corporation of Woodstock, Ill. to the P80/menthol base. Treatment of the subjects who had exhibited vellous new hair growth with the lupine protein formulation produced positive results in thickening of the hair shafts after a period of two to three months.

After experimentation with a range of formula variations it is thought that the synergism of P80 and menthol for stimulating new hair growth can be achieved with menthol contents as low as 6% and as high as 35%, and that any lupine protein content in the range of 15% too 35% will work for thickening the new hair growth.

DETAILED DESCRIPTION OF THE INVENTION

In addressing the aforesaid objectives, the present inventions disclose an improved and simplified formulation for treating hair loss. The present inventions are defined by the following descriptions of components and methods by which the inventions can be made and used. The embodiments shown and described herein are exemplary. Many details are well known in the art, and as such are neither shown nor described.

A preferred embodiment of the inventions is made by the following process: A quantity of 25 ounces of menthol crystals is dissolved in 10 ounces of isopropyl alcohol (70%) by agitating the mixture at approximately 80 degrees F. When the crystals are completely dissolved, 70 ounces of P80 are blended in, with continuing agitation. When the mixture turns translucent, 35 ounces of lupine protein are blended in to complete preparation of 140 ounces of a preferred embodiment of the present invention. The composition is thus, 18% menthol, 7% isopropyl alcohol, 50% P80 and 25% lupine protein.

It has been found that exposure times greater than twenty minutes before shampooing are more effective for the intended purpose of promoting hair growth and, although no definite parameters have been established, a minimum period of one hour before shampooing the treatment out of the subjects hair has been found to be desirable.

The present invention may be altered to provide any desired thickness by the addition of petroleum jelly. Caucasians in general prefer the basic, unaltered composition, while African-Americans, who are accustomed to using heavy pomades, prefer a much thicker solution. To this end, the above described basic composition may be blended with petroleum jelly. The ratio of the basic composition to petroleum jelly may range from 1:1 to 1:3 depending upon the desired consistency. In a preferred embodiment, 140 ounces of the basic composition is blended into 300 ounces of petroleum jelly for a pomade-like consistency.

The embodiments shown and described above are exemplary. It is not claimed that all of the details, parts, elements, or steps described and shown were invented herein. Even though many characteristics and advantages of the present inventions have been described in the accompanying text, the description is illustrative only. Changes may be made in the detail, especially as to additive ingredients, within the scope and principles of the inventions. The restrictive description of the specific examples above do not point out what an infringement of this patent would be, but are to provide at least one explanation of how to use and make the inventions. The limits of the inventions and the bounds of the patent protection are measured by and defined in the following claims.

I claim:

1. A composition for counteracting hair loss comprising:

| Ingredient | Weight % Range |
| --- | --- |
| methol | 5%–25% |
| isopropyl alcohol | 2%–10% |
| polysorbate 60 or 80 | 30%–70% |
| lupine protein | 15%–35%. |

2. A composition for counteracting hair loss comprising:

| Ingredient | Weight % Range |
| --- | --- |
| menthol | 18% |
| isopropyl alcohol | 7% |
| polysorbate 80 | 50% |
| lupine protein | 25%. |

3. A composition for counteracting hair loss comprising the composition according to claim 1 blended with from 1–3 parts of petroleum jelly to one part of the composition.

4. A composition for counteracting hair loss comprising the composition according to claim 2 blended with from 1–3 parts of petroleum jelly to one part of the composition.

5. A method for making a composition for counteracting hair loss comprising the steps of:
   agitating a quantity of from 5 to 25 parts of menthol crystals in 2 to 10 parts of isopropyl alcohol at approximately 80 degrees F. until the menthol crystals dissolve;
   blending 30 to 70 parts of polysorbate 80 or polysorbate 60 into the solution and continuing agitation until it becomes translucent; and
   blending in 15 to 35 parts of lupine protein.

6. The method for making a composition for counteracting hair loss according to claim 5 and further comprising the step of blending one part of the resulting composition with one to three parts of petroleum jelly.

\* \* \* \* \*